United States Patent [19]

Edwards et al.

[11] Patent Number: 5,877,025
[45] Date of Patent: Mar. 2, 1999

[54] GLYCATED PROTEINS ASSAY

[75] Inventors: Raymond Edwards, London; Stuart J.F.E. Blincko, Eastbourne, both of United Kingdom

[73] Assignees: The Royal Hospital of St Bartholomew; The Royal London Hospital; The London Chest Hospital NHS Trust, all of London, England

[21] Appl. No.: 765,461

[22] PCT Filed: Jul. 26, 1995

[86] PCT No.: PCT/GB95/01766

§ 371 Date: Jan. 24, 1997

§ 102(e) Date: Jan. 24, 1997

[87] PCT Pub. No.: WO96/03657

PCT Pub. Date: Feb. 8, 1996

[30] Foreign Application Priority Data

Jul. 27, 1994 [GB] United Kingdom .................. 9415143

[51] Int. Cl.⁶ .................................................. G01N 33/72
[52] U.S. Cl. ............................................................. 436/67
[58] Field of Search ................................................. 436/67

[56] References Cited

U.S. PATENT DOCUMENTS

| | | | |
|---|---|---|---|
| 4,861,728 | 8/1989 | Wagner | 436/501 |
| 5,242,842 | 9/1993 | Sundrehagen | 436/536 |

FOREIGN PATENT DOCUMENTS

| | | |
|---|---|---|
| 3720736 | 1/1989 | Germany . |
| 455225 | 11/1991 | United Kingdom . |
| WO 9013818 | 1/1990 | WIPO . |
| WO 9318407 | 9/1993 | WIPO . |

OTHER PUBLICATIONS

K. Yoshimoto et al., Chemical Abstract of Japanese patent 07063735, Mar. 1995.
E. Schleicher et al., Clinical Chemistry, vol. 36, No. 6, pp. 992–993, No. 0193, Jul. 1990.
Hirsch, R. E., Methods in Enzymology 232, 231–246 (1994).
Wilson, D. H., et al, Clin. Chem. 39/10, 2090–2097 (1993).
Hayashi, Y., et al., Clinica Chimica Acta, 149, No. 1, 13–19 (1985).
Rockey, et al., Ophthalmic Research, vol. 14, No. 6, 416–427 (1982).

Primary Examiner—Mary E. Ceperley

[57] ABSTRACT

A solution phase assay of glycated proteins, such as glycated haemoglobin and plasma-soluble glycated proteins, is carried out by reacting the assay sample with a photoluminescent or chemiluminescent marker compound containing a boronic acid group which reacts selectively with the glycated protein. The luminescence of the marker compound is excited at a wavelength at which it is preferentially quenched by the binding of the marked compound to the glycated protein. The quenching in luminescence gives a measure of the degree of glycation of the glycated proteins.

12 Claims, 5 Drawing Sheets

GLYCATED PROTEINS ASSAY

This invention relates to a method for carrying out an assay for glycated proteins, such as glycated haemoglobin.

The level of glycated haemoglobin in blood is a quantity which is used routinely to assess diabetic patients. High levels of circulating glucose lead to high percentages of glycated proteins. For example, in a non-diabetic person, the percentage of haemoglobin molecules that have been glycated (i.e. to which glucose has bound non-enzymatically) is 4.5–8.0 percent. In a diabetic patient, the levels are much higher (unless treatment is given) and can in severe cases be as much as 20 percent. The level of glycated haemoglobin can therefore be used to monitor treatment.

Virtually all existing methods for the determination of glycated haemoglobin in blood samples depend upon the separation of glycated haemoglobin using for example chromatography, electrophoresis, or solid phase reagents with washing step, prior to measurement.

For example, Wilson et al. (Clin Chem 39/10, 2090–2097 (1993)) describe an assay method for glycated haemoglobin in which the glycated haemoglobin is labelled with a soluble polyanionic affinity reagent, and the anionic complex is then captured with a cationic solid-phase matrix. In this method, the amount of glycated haemoglobin bound to the solid phase matrix is then determined by measuring the quenching by the haemoglobin of the static fluorescence from an added fluorophore.

EP-A-455225 (Nacalai Tesque, Inc.) discloses a method for determining the percentage of glycation of a particular protein. First, the protein is separated from the sample which contains it by preferentially binding it to an antibody which is fixed to a solid support. The support is then washed with labelled boronic acid, which binds to the glycated site on the protein. The liquid and solid phases are separated, and the amount of boronic acid bound to the protein in the solid phase can be measured, thereby allowing the number of glycated protein molecules to be calculated.

U.S. Pat. No. 4,861,728 (Becton, Dickinson & Co) describes a method of determining the percentage of glycosylated haemoglobin in blood. In this method, the total haemoglobin is separated from the liquid phase by binding it to a dipstick, and then the glycosylated haemoglobin is reacted with a dihydroxyboryl reagent conjugated to a fluorescent dye. The absorption of incident light by the dye provides a measure of the amount of glycated haemoglobin. This can be compared with the total amount of haemoglobin, which can be calculated by measuring the absorption of incident light at the absorption wavelength for haemoglobin.

A similar method is described in WO 90/13818 (Axis Research AS). In this method, the glycosylated haemoglobin-containing sample may be haemolysed to liberate any cell bound haemoglobin. Signal-forming molecules conjugated to dihydroxyboryl residues are then reacted preferentially with the glycosylated haemoglobin, the total haemoglobin is separated from the sample, and the amount of glycosylated haemoglobin is measured by measuring the amount of signal-forming molecules.

WO 93/18407 (Abbot Laboratories) is concerned with a method of measuring the amount of glycated haemoglobin in a sample, by reacting the total haemoglobin with a fluorescent marker, and measuring the fluorescent quenching due to the total haemoglobin. The glycated haemoglobin is then separated from the sample by standard methods (ion capture or solid phase separation), and the fluorescent quenching due to it is measured. The two quenching measurements give a percentage of the total haemoglobin which is glycated. The specific binding agent for glycated haemoglobin which is employed is coupled to a latex particle or to polyacrylic acid, in order to achieve the separation of glycated and non-glycated haemoglobin which is essential to the operation of the method.

Separation assays of this kind are time consuming and thus expensive to carry out in practice.

A non-separation assay for glycated albumin is described by Yukiko Hayashi et al. (Clinica Chimica Acta, 149 (1985) 13–19).

The method relies on a specific reaction between the particular fluorophore employed (dansylated phenyl boronic acid) and glycated albumin, which results in the enhancement of the fluorescence of the dansylated phenyl boronic acid. The reason for the enhancement is not explained by the authors, but it clear from the paper that the phenomenon is albumin-specific, i.e., it relies on the specific interaction between albumin and the particular fluorophore employed.

Albumin in blood has a relatively short lifetime, and therefore it is not particularly suitable as an marker for levels of glycation.

Also, because of the nature of the particular fluorophore employed (dansylated phenyl boronic acid), excitation of the fluorophore to produce fluorescence must take place in a region of the spectrum in which proteins also absorb strongly (around 350 nm). This results in a disadvantageously high background signal against which fluorescence enhancement must be measured.

No liquid phase (i.e., non-separation) assay is available for glycated proteins other than albumin.

We have now found that it is possible to carry out a solution phase assay of glycated proteins other than albumin, such as glycated haemoglobin and plasma-soluble glycated proteins, by reacting an assay sample containing the said glycated protein with a photoluminescent or chemiluminescent marker compound (such as a fluorescent compound containing a fluorescein residue), containing a boronic acid group capable of binding with the cis-diol group of the glycated protein, which marker compound is not albumin-specific. The luminescence (typically, fluorescence) of the said residue is then detected at a wavelength such that luminescence is preferentially quenched by the bound glycated protein (e.g., glycated haemoglobin), to an extent which depends upon on the amount of glycated protein which is present (more specifically, on the degree of glycation of the protein present). The amount of the protein present in the solution can thus be determined by the change in luminescence (e.g. fluorescence) caused by such quenching.

Accordingly, in the first aspect of the invention, there is provided a method of carrying out an assay for a glycated protein in a sample, which method comprises     carrying out a reaction in solution between an assay sample and photoluminescent or chemiluminescent marker compound containing a boronic acid group capable of selective binding with the cis-diol group of a glycated protein, which marker compound is not albumin-specific,     exciting the luminescence in the marker compound, and detecting the resulting luminescence,     wherein the nature of the marker and the nature of the excitation are such that the said luminescence occurs at a wavelength at which it is preferentially quenched by the binding of the said marker compound to the said glycated protein, and     determining the quenching in luminescence due to the binding of the said marker compound to the glycated protein.

The term "photoluminescent" as used herein is intended to include both phosphorescence and fluorescence, although it is preferred that the photoluminescent compound is a fluorescent compound. It is preferred that the fluorophore has a principal excitation wavelength of from 450 to 800 nm, (ie. somewhat distant from the principal excitation wavelength of proteins). It is further preferred that the principal fluorescence wavelength is from 450 to 600 nm.

It is particularly preferred that the marker compound contains the residue of a fluorescent compound such as fluorescein or a fluorescein derivative, for example carboxyfluorescein or a chlorofluoreacein. In this case, the excitation wavelength is preferably approximately 480 nm, and the fluorescence is preferably detected at approximately 520 nm.

Other complex organic molecules which are chemiluminescent or phosphorescent rather than fluorescent can also be used as luminescent markers in the method of the invention, provided that their chemiluminescence or phosphorescence can be selectively quenched by covalent bonding to a glycated protein such as glycated haemoglobin.

Other suitable fluorophores are the following (the figures shown in parentheses are the principal excitation and fluorescence wavelengths)

naphthofluorescein ($\lambda$ex 600 nm $\lambda$em 672 nm)

eosin ($\lambda$ex 522 nm $\lambda$em 543 nm)

erythrosin ($\lambda$ex 528 nm $\lambda$em 553 nm)

coumarin and umbelliferone ($\lambda$ex 360 nm $\lambda$em 460 nm) derivatives rhodamine derivatives
  e.g. Rhodamine B ($\lambda$ex 550 nm $\lambda$em 585 nm)
  tetramethyl rhodamine ($\lambda$ex 540 nm $\lambda$em 570 nm)

texas red derivatives ($\lambda$ex 589 nm $\lambda$em 615 nm)

lucifer yellow derivatives ($\lambda$ex 420 nm $\lambda$em 535 nm)

Various BODIPY ($4_1$4-difluoro-4-bora-$3a_1$4a diaza-s-indacine) derivatives

NBD-halide (4-halogeno-7-nitrobenzo-2-oxa-$1_1$3-diazole) derivatives

Lanthanide chelate derivatives

Transition metal chelate derivative, e.g. Ru tris phenanthroline or Ru tris bipyridyl derivatives

Phycobiliprotein derivatives

The group capable of selective binding with a cis-diol is a boronic acid group. Boronic acids are known to form covalent (but not particularly stable) bonds with the cis-diol groups of glycated proteins. The bonds formed are, however, sufficiently stable to enable the assay determination to be made in solution.

Haemoglobin is a known quencher of fluorescence. If a fluorescent molecule is bound covalently and specifically to glycated haemoglobin, but not to non-glycated haemoglobin molecules, it is possible to derive, without separation, a measure of the level of haemoglobin glycation directly from the measured amount of fluorescence quenching. High levels of glycated haemoglobin will quench the fluorescent signal more than low levels. The same effect is observed with other glycated proteins, for example, plasma-soluble or serum-soluble glycated proteins.

The principal application of the assay method of the invention is in the measurement of glycation levels of blood proteins linked to the control of diabetes.

The preparation of boronic acid derivatives of fluorescein is described for example, in DE-A-3720736. The derivative employed in the present invention is preferably a compound of the formula F—A—B $(OH)_2$, wherein F is a fluorescein residue, and A is a suitable linking group to link the fluorescein residue to the boronic acid group. In a preferred embodiment, the linking group A may be a group of the formula —NH.CS.NH.Ph—, wherein Ph is a phenyl group. In a particular preferred embodiment, the compound has the formula:

A number of preferred embodiments of the invention are described in the following Examples.

The following buffers were employed in the Examples:
Carbonate Buffer
  4.2 ml of sodium hydrogen carbonate was dissolved in 500 ml distilled water and the pH adjusted to 9.0 by addition of solid sodium carbonate.
Assay buffer
  7.51 g glycine and 10.16 g magnesium chloride hexahydride were dissolved in 1000 ml distilled water. The pH of the solution was adjusted to 8.5 by addition of 1.0M sodium hydroxide solution.
Sample lysing buffer
  2 ml of a lysing detergent (TM TRITON X-100) was dissolved in 100 ml of assay buffer.

EXAMPLE 1

A fluorescein-boronic acid compound of formula I above was prepared by the following method. Fluorescein isothiocyanate (10 mg), m-aminophenylboronic acid (4 mg) and triethylamine (3 mg) were mixed in 0.9 ml methanol, and 0.1 ml distilled water. The mixture was stirred for one hour at room temperature and then a further 4 mg of m-aminophenyl-boronic acid was added. Stirring was continued for a further hour, and the solution was then purified by thin layer chromatography (eluent dichloromethane:methanol, 9:1).

The green band (Rf 0.2–0.3) was eluted from the silica with methanol, and the resultant solution stored at −20° C. 0.5 ml of the methanol solution was diluted in 4.5 ml carbonate buffer and the optical density recorded at 492 nm.

It was established that the optical density was proportional to the concentration, the optical density being $8.78 \times 10^4 \times$ the concentration in mols/liter.

The solution was diluted in the assay buffer to a concentration of 5 nmols/l.

EXAMPLE 2
Glycated Haemoglobin Assay

Whole blood samples were collected from patients and stored at 4° C. with an EDTA anti-coagulant.

The samples were centrifuged at 3000 rpm for 5 minutes. 50 μl aliquots were added to 450 μl sample lysing buffer and vortex mixed.

20 μl aliquots of the lysate were added to 2 ml samples of the fluorescent tracer solution prepared in Example 1, vortex mixed, and left in the dark for 30 minutes at room temperature. The samples were then read on a fluorimeter (Perkin Elmer LS20™ equipped with a flow cell), at 520 nm (excitation frequency 480 nm). Similar runs were made without sample addition as controls and the total quenching for each of the sample runs was determined by difference.

Total haemoglobin content of each of the measured samples was also quantified by UV spectrophotometry using a CECIL 300™ UV instrument at 405 nm, and the ratio calculated of the level of fluorescence quenching to the total haemoglobin content (as measured by ΔF/OD, where ΔF is the decrease in signal measured at 520 nm caused by quenching, and OD is the optical density measured at 405 nm).

Figure 1:
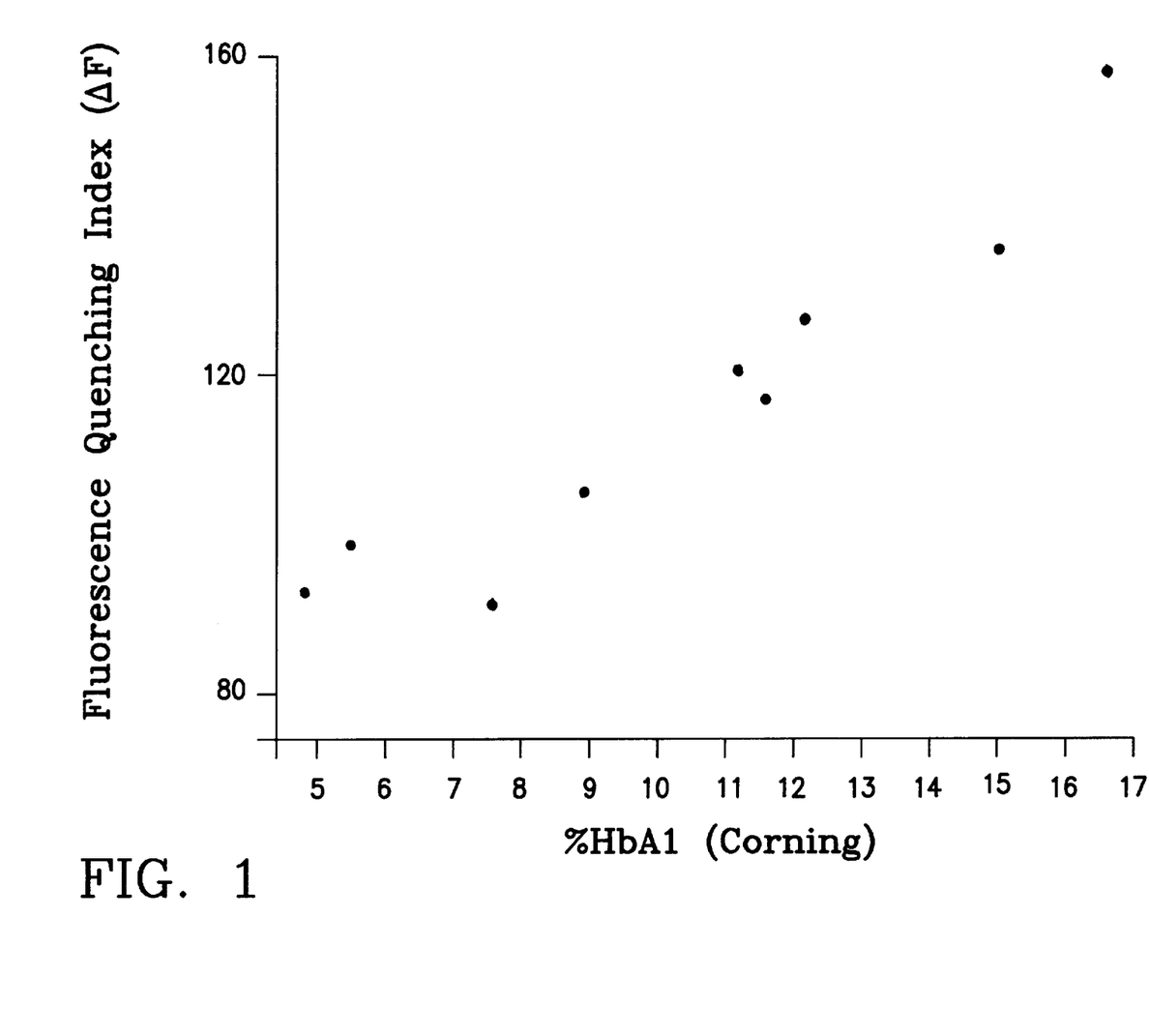
FIG. 1 is a graph of $\Delta F$ versus % HbA1 (Corning test kit) and depicts results of Example 2.
Figure 2:
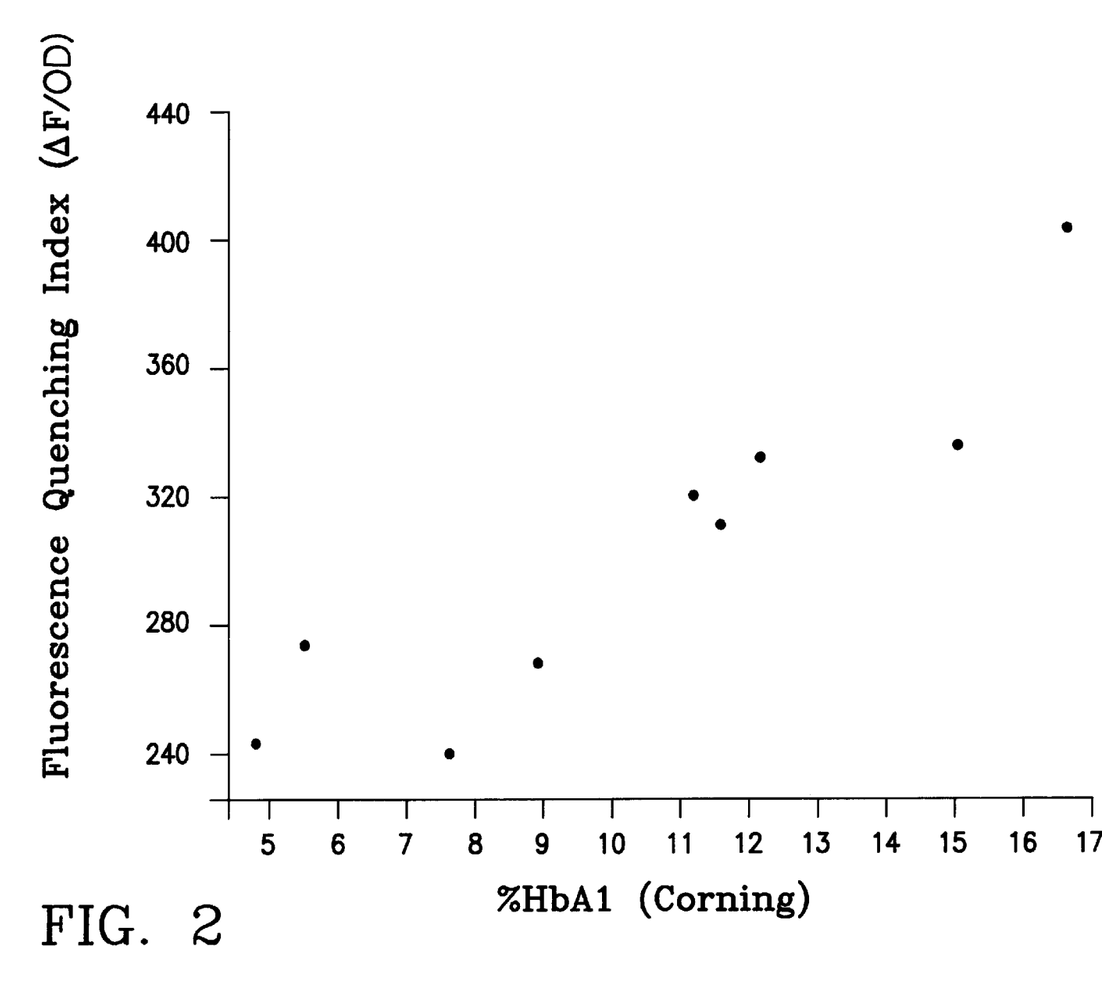
FIG. 2 is a graph of $\Delta F/OD$ versus % HBA1 (Corning test kit) and depicts results of Example 2.

The glycated haemoglobin level (% HbA1) of the same blood samples was measured using a commercially available test kit (Corning), and the results are tabulated in Table I. FIGS. 1 and 2 respectively show graphically the correlation between ΔF, and % HbA1, and between ΔF/OD, and % HbA1. The clear correlation in FIG. 2 demonstrates that the single phase fluorescence quenching method of the present invention may be used as an accurate measure of glycated haemoglobin level of a blood sample. The correlation in FIG. 1 illustrates that ΔF alone may in some circumstances (namely, when the total haemoglobin level is known not to differ widely between samples) be a sufficiently accurate measure of HbAl content.

EXAMPLE 3
Plasma Assay

Whole blood samples were collected from patients as in Example 2 and stored at 4° C. with an EDTA anti-coagulant.

The samples were centrifuged at 3000 rpm for 5 minutes. 50 μl aliquots of the supernatant plasma was diluted to 500 μl with 450 the same buffer as used in Example 2, and vortex mixed.

20 μl aliquots of the mixed solution were added to 2 ml samples of solution prepared as in Example 1, vortex mixed, and left in the dark for 30 minutes at room temperature. The samples were then read as in Example 2.

Figure 3:
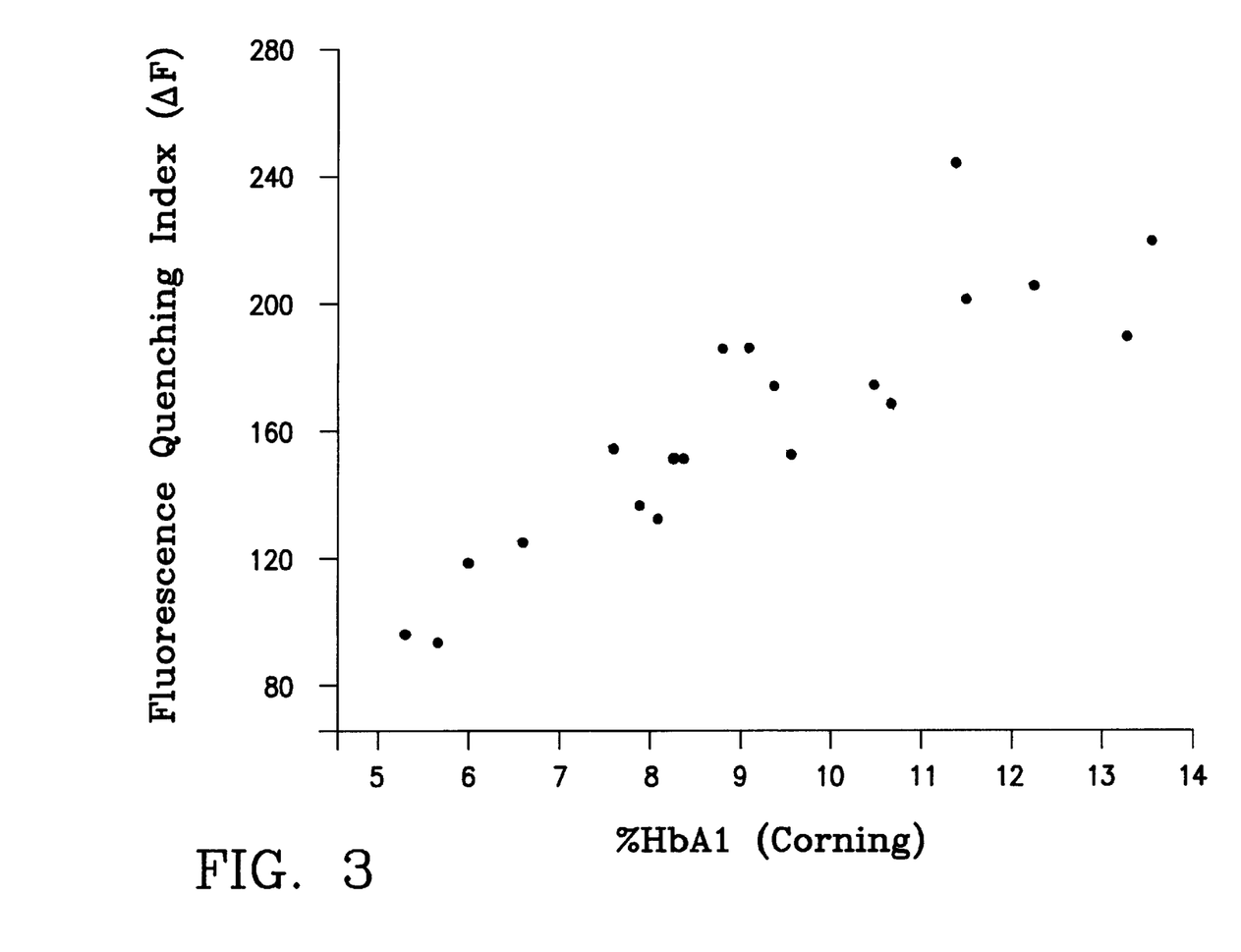
FIG. 3 is a graph of $\Delta F$ versus % HbA1 (Corning test kit) and depicts results of Example 3.

The glycated haemoglobin level of the original blood samples was again measured using the Corning test kit. The results are tabulated in Table 2. The same results are shown graphically in FIG. 3.

In this case, fluorescence quenching is not caused directly by glycated haemoglobin, since the level of glycated haemoglobin in the plasma sample is negligible. The quenching is clearly caused by the presence in the plasma of some other glycated protein. Table 2 and FIG. 3 clearly illustrate that a strong correlation also exists between the glycated haemoglobin level in the original blood samples and fluorescence quenching caused by the presence of this material in the supernatant plasma. For clinical purposes, it is not necessary to know the precise nature of glycated plasma protein which causes the fluorescence quenching, provided that the amount of fluorescence quenching correlates with the level of glycated haemoglobin level in the original blood samples.

EXAMPLE 4
Whole blood

Whole blood samples were collected from patients and stored at 4° C. with an EDTA anti-coagulant.

The samples were rotated for 10 minutes. 50 μl aliquots were added to 450 μl sample lysing buffer and vortex mixed. These were left at room temperature for 1 hr.

20 μl aliquots of the lysate were added to 2 ml of the fluorescent tracer solution as prepared in Example 1, vortex mixed, and left in the dark for 30 minutes at room temperature. The samples were then read on a fluorimeter (Perkin Elmer LS20™ equipped with a flow cell), at 520 nm (excitation frequency 480 nm). Similar runs were made without sample addition as controls and the total quenching for each of the sample runs was determined by difference.

Figure 4:
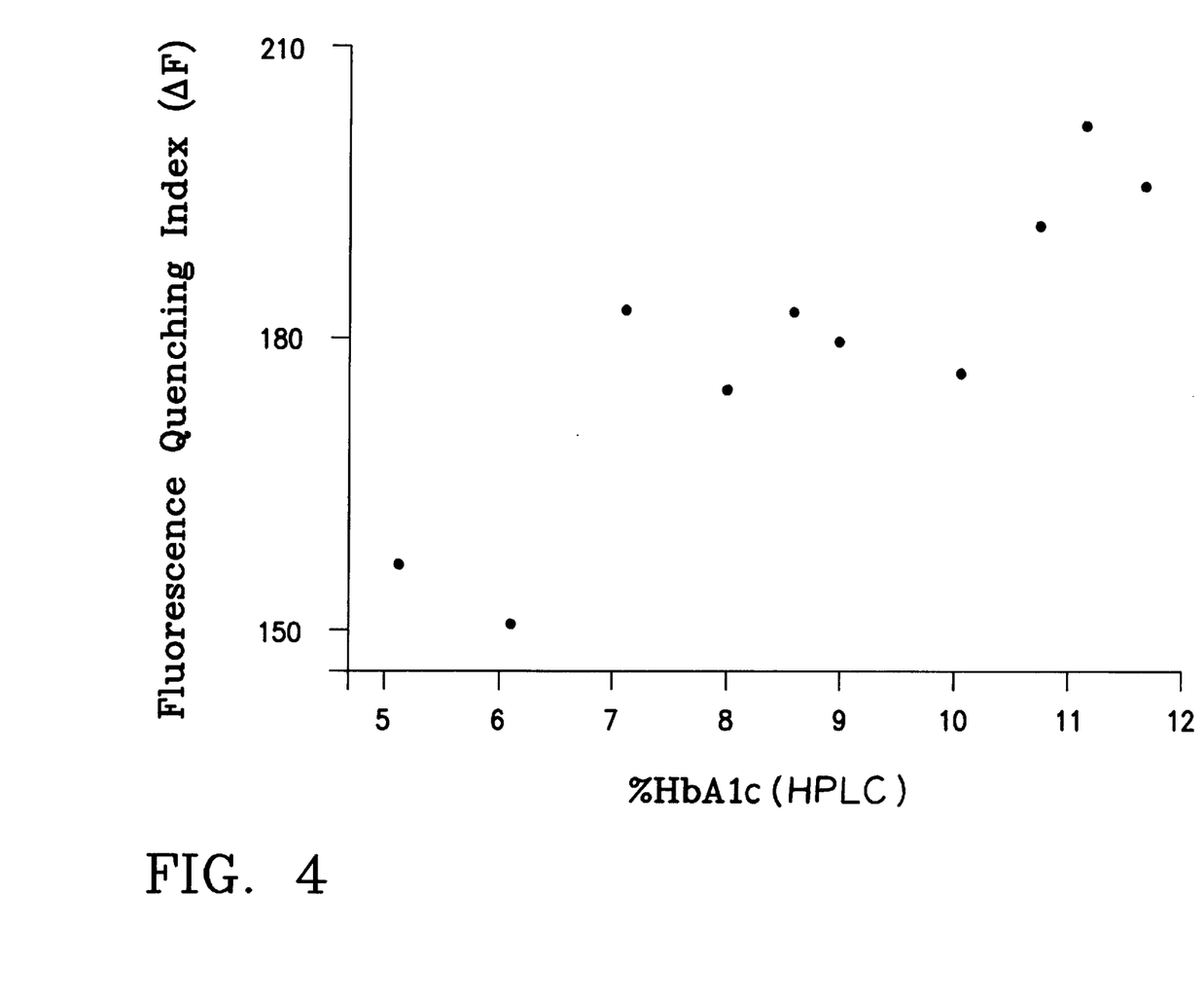
FIG. 4 is a graph of $\Delta F$ versus % HbA1 (HPLC) and depicts results of Example 4.

The glycated haemoglobin level (% HbA1c) of the same blood samples was measured using a commercially available Table 3. FIG. 4 shows graphically the correlation between ΔF and % HbA1c. The correlation shown in FIG. 4 demonstrates that the single phase fluorescence quenching method of the present invention may be used as an accurate measure of glycation level of a blood sample.

EXAMPLE 5
Filter paper blood spot

30 μl samples were collected from patients, spotted onto absorbent filter paper and stored at room temperature.

Filter paper blood spots, cut using a hole-punch, were added to 2 ml of the fluorescent tracer solution as prepared in Example 1, vortex mixed and left in the dark for 60 minutes at room temperature. The samples were then vortex mixed and read on a fluorimeter (Perkin Elmer LS20™ equipped with a flow cell), at 520 nm (excitation frequency 480 nm). Similar runs were made without sample addition as controls and the total quenching for each of the sample runs was determined by difference.

Figure 5:
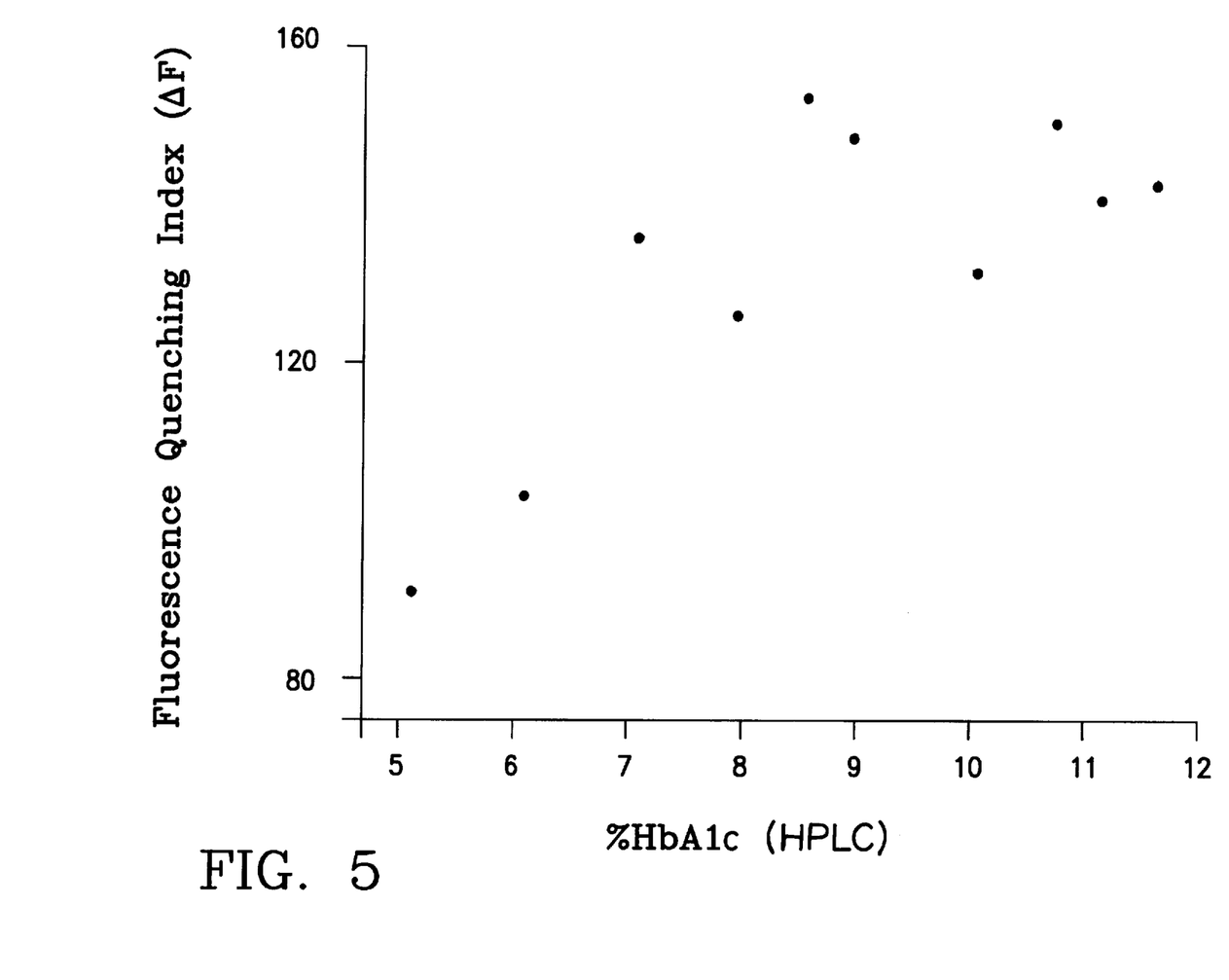
FIG. 5 is a graph of $\Delta F$ versus % HbA1 (HPLC) and depicts results of Example 5.

The glycated haemoglobin level (% HbA1c) of the same blood samples was measured using a commercially available test kit (HPLC method) and the results are tabulated in Table 4. FIG. 5 shows graphically the correlation between ΔF and % HbA1c. The correlation in FIG. 5 demonstrates that the single phase fluorescence quenching method of the present invention may be used as an accurate measure of glycation level of a blood spot sample.

EXAMPLE 6
Use of other fluorophores

An umbelliferone-boronic acid compound was prepared by the following method.

7-hydroxy-4-methylcoumarin-3-acetic acid succinimidyl ester (10 mg) in dimethylformamide (100 μl), and m-aminophenylboronic acid (5 mg) in pH 9.0 carbonate buffer (100 μl) were mixed and stirred for 1 hour in the dark. The solution was purified by thin layer-chromatography (eluent chloroform:methanol, 4:1).

A band (Rf 0.79–0.82) was eluted from the silica with methanol. An aliquot of the methanol solution was diluted tenfold in carbonate buffer pH 9.0. The concentration of product was calculated using the optical density at 360 nm and an extinction coefficient of 17,000.

The quenching of the prepared umbelliferone-boronic acid derivative was measured using the procedure given in Example 3, but with 100 nM concentration of the umbelliferone-boronic acid derivative and 200 μl aliquots of samples diluted tenfold. The results are shown in Table 5.

It will of course be understood that the invention may be put into practice in many other ways in addition to those specifically outlined above. In particular, the nature of the fluorophore may be varied, appropriate changes being made to the excitation frequency.

TABLE 1

| Sample | Meas. (F.)[3] | Δ F. | Hb OD | Ratio | Corning[1] |
|---|---|---|---|---|---|
| 1 | 724.50 | 94.30 | 0.380 | 248.16 | 4.80 |
| 1 | 728.20 | 90.60 | 0.380 | 238.42 | 4.80 |
| 2 | 719.30 | 99.50 | 0.359 | 277.16 | 5.50 |
| 2 | 721.40 | 97.40 | 0.359 | 271.31 | 5.50 |
| 3 | 727.80 | 91.00 | 0.380 | 239.47 | 7.60 |
| 3 | 726.80 | 92.00 | 0.380 | 242.11 | 7.60 |
| 4 | 711.70 | 107.10 | 0.396 | 270.45 | 8.90 |
| 4 | 715.20 | 103.60 | 0.396 | 261.62 | 8.90 |
| 5 | 696.50 | 122.30 | 0.378 | 323.54 | 11.20 |
| 5 | 698.70 | 120.10 | 0.378 | 317.72 | 11.20 |
| 6[2] | 701.60 | 117.20 | 0.376 | 311.70 | 11.60 |
| 6[2] | 700.50 | 118.30 | 0.376 | 314.63 | 11.60 |
| 7 | 691.60 | 127.20 | 0.382 | 332.98 | 12.20 |
| 7 | 691.30 | 127.50 | 0.382 | 333.77 | 12.20 |
| 8 | 682.00 | 136.80 | 0.403 | 339.45 | 15.10 |
| 8 | 683.20 | 135.60 | 0.403 | 336.48 | 15.10 |
| 9 | 658.70 | 160.10 | 0.391 | 409.46 | 16.70 |
| 9 | 661.20 | 157.60 | 0.391 | 403.07 | 16.70 |

[1]results of Corning test are given as % HbA1
[2]Sickle cell sample
[3]Total fluorescence (no sample) value = 818.80

TABLE 2

| Sample | Meas. (F.) | Δ F. | Corning |
|---|---|---|---|
| 1 | 700.2 | 95.1 | 5.3 |
| 1 | 697.6 | 97.7 | 5.3 |
| 2 | 705.4 | 89.9 | 5.7 |
| 2 | 697.6 | 97.7 | 5.7 |
| 3 | 673.4 | 121.9 | 6.0 |
| 3 | 679.6 | 115.7 | 6.0 |
| 4 | 669.1 | 126.2 | 6.6 |
| 4 | 670.6 | 124.7 | 6.6 |
| 5 | 638.0 | 157.3 | 7.6 |
| 5 | 639.0 | 156.3 | 7.6 |
| 6 | 656.4 | 138.9 | 7.9 |
| 6 | 660.2 | 135.1 | 7.9 |
| 7 | 657.3 | 138.0 | 8.1 |
| 7 | 667.5 | 127.8 | 8.1 |
| 8 | 646.7 | 148.6 | 8.3 |
| 8 | 638.0 | 157.3 | 8.3 |
| 9 | 638.0 | 157.3 | 8.4 |
| 9 | 645.9 | 149.4 | 8.4 |
| 10 | 609.7 | 185.6 | 8.8 |
| 10 | 604.5 | 190.8 | 8.8 |
| 11 | 608.5 | 186.8 | 9.1 |
| 11 | 605.3 | 190.0 | 9.1 |
| 12 | 619.7 | 175.6 | 9.4 |
| 12 | 618.1 | 177.2 | 9.4 |
| 13 | 638.6 | 156.7 | 9.6 |
| 13 | 643.0 | 152.3 | 9.6 |
| 14 | 613.9 | 181.4 | 10.5 |
| 14 | 622.0 | 173.3 | 10.5 |
| 15 | 620.7 | 174.6 | 10.7 |
| 15 | 629.3 | 166.0 | 10.7 |
| 16 | 543.3 | 252.0 | 11.4 |
| 16 | 551.1 | 244.2 | 11.4 |
| 17 | 588.4 | 206.9 | 11.5 |
| 17 | 593.7 | 201.6 | 11.5 |
| 18 | 585.1 | 210.2 | 12.3 |
| 18 | 587.2 | 208.1 | 12.3 |
| 19 | 602.4 | 192.9 | 13.3 |
| 19 | 603.6 | 191.7 | 13.3 |
| 20 | 572.8 | 222.5 | 13.6 |
| 20 | 571.3. | 224.0. | 13.6. |

Total fluorescence (no sample) value = 795.30

TABLE 3

| SAMPLE | % HbA1cc | FLUORESCENCE INDEX | Δ F. |
|---|---|---|---|
| 1 | 5.1 | 592.8 | 157.2 |
| 2 | 6.2 | 598.8 | 151.2 |
| 3 | 7.1 | 567.2 | 182.8 |
| 4 | 8.0 | 575.1 | 174.9 |
| 5 | 8.6 | 566.6 | 183.4 |
| 6 | 9.0 | 569.6 | 180.4 |
| 7 | 10.1 | 572.7 | 177.3 |
| 8 | 10.8 | 557.9 | 192.1 |
| 9 | 11.2 | 548.0 | 202.0 |
| 10 | 11.7 | 554.4 | 195.6 |

TOTAL FLUORESCENCE = 750

TABLE 4

| SAMPLE | % HbA1cc | FLUORESCENCE INDEX | Δ F. |
|---|---|---|---|
| 1 | 5.1 | 560 | 90 |
| 2 | 6.2 | 548 | 102 |
| 3 | 7.1 | 514 | 136 |
| 4 | 8.0 | 525 | 125 |
| 5 | 8.6 | 496 | 154 |
| 6 | 9.0 | 502 | 148 |
| 7 | 10.1 | 518 | 132 |
| 8 | 10.8 | 499 | 151 |
| 9 | 11.7 | 510 | 140 |

TOTAL FLUORESCENCE = 650

TABLE 5

| SAMPLE | (approx) % HbA1c | FLUORESCENCE QUENCHING INDEX (Δ F.) |
|---|---|---|
| High | 13 | 61 |
| Medium | 7 | 53 |
| Low | <1 | 42 |

We claim:

1. A method of carrying out an assay for a glycated protein in a sample, which method comprises:
   carrying out a reaction in solution between an assay sample and photoluminescent or chemiluminescent marker compound containing a boronic acid group capable of selective binding with the cis-diol group of a glycated protein, but not exclusively with albumin, and, without separation of the reaction product from the solution, exciting the luminescence in the marker compound, and detecting the resulting luminescence, wherein the nature of the marker and the nature of the excitation are such that the said luminescence occurs at a wavelength at which it is preferentially quenched by the binding of the said marker compound to the said glycated protein, and
   determining the quenching in luminescence due to the binding of the said marker compound to the glycated protein.

2. A method as claimed in claim 1, wherein the glycated protein is glycated haemoglobin, or a plasma-soluble glycated protein.

3. A method as claimed in claim 1 or claim 2, wherein the sample is a blood sample, a plasma sample or a serum sample.

4. A method as claimed in claim 1, wherein the photoluminescent compound is a fluorescent compound.

5. A method as claimed in claim 4, wherein the fluorescent compound has a principal excitation wavelength of at least 450 nm.

6. A method as claimed in claim 5, wherein the fluorescent compound has a principal excitation wavelength of from 450 to 800 nm.

7. A method as claimed in any one of claims 4 to 6, wherein the fluorescent compound has a principal luminescence wavelength of from 450 to 600 nm.

8. A method as claimed in claim 7, wherein the said principal luminescence wavelength is approximately 520 nm.

9. A method as claimed in claim 4, wherein the fluorescent compound contains a fluorescein residue.

10. A method as claimed in claim 9, wherein the fluorescent compound is a group of the formula F—NH—CS—NH—Ph—B(OH)$_2$, wherein Ph is a phenyl group and F is a fluorescein residue.

11. A method as claimed in claim 9, wherein the fluorescent compound is a compound of the formula:

12. A method as claimed in claim 1, wherein the glycated protein is glycated haemoglobin.

* * * * *

UNITED STATES PATENT AND TRADEMARK OFFICE
CERTIFICATE OF CORRECTION

PATENT NO. : 5,877,025
DATED : March 2, 1999
INVENTOR(S) : Raymond Edwards, et al.

It is certified that error appears in the above-identified patent and that said Letters Patent is hereby corrected as shown below:

On the title page, change item [73] to be:

--Assignee: THE ROYAL HOSPITAL OF ST BARTHOLOMEW, THE ROYAL LONDON HOSPITAL AND THE LONDON CHEST HOSPITAL NHS TRUST, of London, England.--

Signed and Sealed this

Twenty-second Day of June, 1999

*Attest:*

Q. TODD DICKINSON

*Attesting Officer*  Acting Commissioner of Patents and Trademarks